(12) United States Patent
Armbruster et al.

(10) Patent No.: US 11,043,292 B2
(45) Date of Patent: Jun. 22, 2021

(54) APPARATUS AND METHOD FOR PRODUCING A MEDICAL REPORT

(71) Applicant: SMART REPORTING GMBH, Munich (DE)

(72) Inventors: Marco Armbruster, Munich (DE); Jonathan Berroth, Pritzwalk (DE)

(73) Assignee: SMART REPORTING GMBH, Munich (DE)

( * ) Notice: Subject to any disclaimer, the term of this patent is extended or adjusted under 35 U.S.C. 154(b) by 494 days.

(21) Appl. No.: 15/549,568

(22) PCT Filed: Feb. 22, 2016

(86) PCT No.: PCT/EP2016/053678
§ 371 (c)(1),
(2) Date: Aug. 8, 2017

(87) PCT Pub. No.: WO2016/135100
PCT Pub. Date: Sep. 1, 2016

(65) Prior Publication Data
US 2018/0039760 A1     Feb. 8, 2018

(30) Foreign Application Priority Data
Feb. 23, 2015   (DE) .................... 10 2015 102 555.8

(51) Int. Cl.
*G16H 15/00*     (2018.01)
*G16H 10/20*     (2018.01)
(Continued)

(52) U.S. Cl.
CPC ............. *G16H 15/00* (2018.01); *G06F 40/14* (2020.01); *G06F 40/186* (2020.01); *G16H 10/20* (2018.01)

(58) Field of Classification Search
None
See application file for complete search history.

(56) References Cited

U.S. PATENT DOCUMENTS

| 6,684,188 B1 | 1/2004 | Mitchell et al. .................. 705/3 |
| 7,496,837 B1 * | 2/2009 | Larcheveque .......... G06F 40/14 715/237 |

(Continued)

*Primary Examiner* — Aryan E Weisenfeld
*Assistant Examiner* — Karen A Hranek
(74) *Attorney, Agent, or Firm* — Stein IP, LLC

(57) ABSTRACT

The present invention provides an apparatus for electronically producing a at least a part of a medical report. The apparatus implements a question tree (Q) comprising a plurality of mostly interrelated question nodes, and a report node tree (RN) comprising a plurality of report nodes, wherein at least one of the report nodes comprises and/or represents a text template. The apparatus further comprising an engine adapted to receive inputs, store the input relating to a selected question node, identify at least one affected report node associated with the selected question node, and change a property, in particular a visibility property, of at least one of the at least one affected report nodes, and preferably, insert and/or store the received input in either the at least one affected report node and/or the selected question node. The present invention also provides a method for electronically producing a medical report, and a computer readable device for implementing the method.

12 Claims, 6 Drawing Sheets

(51) Int. Cl.
  *G06F 40/186* (2020.01)
  *G06F 40/14* (2020.01)

(56) References Cited

U.S. PATENT DOCUMENTS

| | | | |
|---|---|---|---|
| 2002/0111932 A1* | 8/2002 | Roberge | G06F 3/0482 |
| 2004/0168119 A1 | 8/2004 | Liu et al. | 715/501.1 |
| 2005/0039107 A1* | 2/2005 | Hander | G06F 40/56 |
| | | | 715/256 |
| 2005/0114283 A1 | 5/2005 | Pearson et al. | 706/50 |
| 2006/0020886 A1* | 1/2006 | Agrawal | G06F 17/243 |
| | | | 715/256 |
| 2008/0133572 A1 | 6/2008 | Verhey-Henke et al. | 707/102 |
| 2011/0231207 A1 | 9/2011 | Easterly | 705/3 |
| 2012/0084096 A1 | 4/2012 | Wang | 705/2 |
| 2013/0006654 A1 | 1/2013 | Hermans | 705/2 |
| 2013/0246095 A1* | 9/2013 | Mailhot | G06Q 10/10 |
| | | | 705/3 |
| 2014/0052444 A1 | 2/2014 | Roberge | 704/243 |
| 2014/0281917 A1 | 9/2014 | Alpern et al. | 715/234 |
| 2014/0344679 A1 | 11/2014 | Larsen et al. | 715/256 |
| 2014/0359421 A1 | 12/2014 | Allen et al. | 715/230 |

\* cited by examiner

| QuID | InID | QNrelID | Condition |
|------|------|---------|-----------|
| Q1 | Y/N | QS | - |
| Q11 | List3 | Q1 | Y |
| Q111 | Free | Q11 | ANY |
| Q2 | NUM | QS | 2 |
| Q21 | List5 | Q2 | NUM1 |
| Q21' | List5 | Q2 | NUM2 |
| Q211 | 1,0,-1 | Q21 | ANY |

| RnID | QuID | Condition | Action |
|------|------|-----------|--------|
| R1 | Q1 | Y | Display |
| R1 | Q1 | N | Hide |
| R11a | Q11 | List1 | Func #1 |
| R11b | Q11 | List2 | Func #1 |
| R11c | Q11 | List3 | Func #1 |
| R111 | Q111 | Free | Func #2 |
| R2 | Q2 | NUM | Dup |
| R21 | Q21 | ListFree | Display |
| R21' | Q21 | ListFree | Display |
| R211a | Q211 | 1 | Display |
| R211b | Q211 | -1 | Display |

Fig. 3b

APPARATUS AND METHOD FOR PRODUCING A MEDICAL REPORT

CROSS-REFERENCE TO RELATED APPLICATIONS

This application is a national stage of International Application No. PCT/EP2016/053678 filed Feb. 22, 2016, which claims the benefit of German Application No. 10 2015 102 555.8 filed Feb. 23, 2015 in the German Patent Office, the disclosures of which are incorporated herein in their entireties by reference.

DESCRIPTION

The invention relates to the production of a medical report and, more specifically, provides an apparatus and method for electronically producing at least a part of a medical report, in addition to a computer readable device for performing the method.

When a patient is examined by a medical professional, vast amounts of data are often collected. This can include many different types of data depending upon the examination procedures that the patient is subjected to; for example, the data may be observations recorded by the medical professional such as physical symptoms, measurement results from various medical devices, data from images such as CT, or MRI examinations or reports regarding performed surgery or medical interventions.

Previously, data has been collected in a number of manners, primarily using handwritten notes, keyboards, dictation devices or via speech recognition. This data is often required to be presented in the form of a medical report, which can be used to summarise the patient's current condition or to present information obtained by a specialist to other medical professionals. These medical reports can often be time consuming to produce and can also vary in style and form depending upon the medical professional generating the report. In some cases, this can lead to ambiguous and/or inaccurate medical reports, in some cases even with relevant data being missed from the medical report.

Standard templates for medical reports have been employed previously, wherein a medical professional must fill in the template using manually entered text. US 2006/0020886 A1 describes such a method, for example.

However, there exists a need for producing customised medical reports containing relevant information pertaining to each patient and/or each medical procedure. There also exists a need to provide such reports in a time and resource efficient manner and in a way that enables information to be readily located from the medical report even during generation of the report.

Furthermore, such reports should be very responsive when a user is working with it. Usability of a report is increased if the user immediately sees a result which he has generated by an input. A high responsiveness should be available even if the report is used in a client-server environment. In this environment bandwidth might be limited. Furthermore, the available network might have a high latency.

The problem is solved by an apparatus for electronically producing at least a part of a medical report, the apparatus and/or a component of the apparatus implementing:

a question tree, the question tree comprising a plurality of question nodes, at least some of the question nodes representing a question, wherein at least one of the questions is related to and depends upon the answer of another of the questions;

a report node tree comprising a plurality of report nodes, wherein at least one of the report nodes comprises and/or represents a text template; and an engine adapted to
receive inputs, at least one of the inputs relating to the question of a selected question node of the plurality of question nodes,
store the input in the selected question node and/or associated therewith,
Identify at least one affected report node associated with the selected question node,
change a property, in particular a visibility property, of at least one of the at least one affected report nodes, and preferably, insert and/or store the received input in either the at least one affected report node and/or the selected question node.

The present invention provides an apparatus for electronically producing a medical report preferentially by answering a series of typically interrelated questions, which are represented in a hierarchical, preferably tree-like data structure, and identifying relevant text templates or other objects arranged in a second hierarchical, preferably tree-like data structure corresponding to and/or being derived from the answers given.

The questions are preferably presented in the form of question nodes that form a question tree, although not every question node may relate to a question. As used herein, the term question should be understood as including direct questions, e.g., "Where is the tumour located?", and/or more general statements designed to prompt a user to insert information, e.g., "Location of tumour". In addition, the tree-like data structure may have one or more starting points for branches of the tree; that is, where the answer to one question leads to a further question being asked. Preferably, however, all the questions are commonly related to a global theme, e.g., broken bone, tumour, etc. Thus, in one interpretation, the questions are interrelated to a common theme, but not all questions are related to each other.

The text templates are preferably presented in the form of report nodes that form a report node tree, although not every report node may contain a text template. Text template should herein be understood as a text and/or object based element. The text based element is, for example, a text string which can comprise one character, many characters, one word, many words, one sentence, many sentences, or any combination. The text template may also be a blank text string, i.e., comprise blank spaces as characters. These can be "filled in" as appropriate depending upon the received input. Additionally, the text template can comprise objects and/or functions, either alone or in combination with text based element(s). The report nodes may correspond to one or more of a plurality of question nodes. Each report node may be provided with one or more properties, preferably a visibility property. Initially, the visibility property is typically set to hide the report nodes from view.

The apparatus comprises an engine which receives inputs relating to the questions of the question tree. Specifically, an input relating to a question node may be input to the engine. The input is preferably either an element that is selected from a list provided at the question node, i.e., a YES/NO or a), b), c), or is input by a user of the apparatus. The input may be text-based which also includes numerical values.

The engine might be hosted on the client side of the system. Thus, the inventive data structures for questions and text allow loading most or all of the relevant data at the very beginning. Afterwards, the user interaction can take place without any further or very little use of a network resource. Accordingly, the inventive apparatus provide offline capability. E.g. the user might disconnect and continue working with the report.

Also, the inventive data structure allows organizing the input of the user in a very efficient manner. Entries can be processed immediately and lead to text results which can be cross-checked. With the given data trees complex conditions can be implemented for generating text, whereby the implementation requires very little calculation power.

The relationship between the question and report trees allows fast interaction between these trees and thus ensures high responsiveness. Also, the report tree structure allows modifying text of a report manually without having to break up the relationship between the question nodes and the report nodes such that changing answers to certain questions at a later stage will not affect the functionality of the report.

In combination with receiving the input, the engine is preferably adapted to store the input. Preferably, the input is stored either in the report nodes affected when answering the question or in the nodes of the question tree. A memory associated with the respective trees may also be provided. Thus, no separate data structure for storing the inputs needs to be implemented. This saves memory and resource when several inputs need to be processed. The engine may also change a stored property of the question and/or report nodes when storing an input.

The engine further identifies at least one affected report node of the report tree. In one embodiment, the engine (or associated memory) comprises a relationship table that indicates a relationship between question nodes and report nodes. The relationship table may also comprise an indication as to when the relationship is valid, i.e., the relationship may depend upon the received input given in answer to the question corresponding to the question node. Using this table, the engine may identify which of the report nodes are affected or influenced by the input relating to the specific question node. The relationship can also be stored within the nodes, e.g. by using pointers or IDs. In an alternative embodiment the relationship between question nodes and report nodes can also be implemented by matching attributes, e.g. names or identifiers, of the question node and the report node. The respective matching can be implemented by the engine at runtime.

Once the relevant report nodes have been identified, the engine changes a property of the report nodes, preferably a visibility property. In this way, report nodes that are initially provided hidden from view can be displayed upon the engine receiving an input corresponding to the relevant report nodes.

Accordingly, a medical report may then be dynamically generated by answering the questions corresponding to the question nodes. This is particularly advantageous as the user of the apparatus is provided only with the information that is directly of relevance and in a controlled manner, i.e., by answering one question at a time. The report may subsequently be dynamically altered depending upon the inputs, meaning that the text of text templates can be displayed and removed depending upon the answers to the questions. In this way, fewer mistakes when preparing the medical report can occur by the user being overloaded with information or forgetting to insert other information. Moreover, the report can be provided in a more standardised manner meaning that any medial professional looking at the report may be able to readily identify the relevant information.

In a further embodiment, the engine is adapted to display at least parts of the text template of at least one report node based on the property, in particular a/the visibility property, of at least one report node, the displayed text template forming at least a part of the medical report.

In this regard, the engine causes text and/or objects forming the text template to be displayed to a user, wherein the displayed text forms at least a part of the medical report. Additional text could also be included in the report, as could the results of certain calculations. Moreover, only parts of the text template may be displayed, which is particularly relevant when the final form of the text template may depend upon additional inputs received in relation to other question nodes. In this way, the user can be presented with a hint as to what other additional inputs must be provided to complete the text template.

In an additional or alternative configuration, the apparatus further comprises a memory for storing a plurality of relationships, the relationships including:

a relationship between at least one question node and at least one report node; and/or relationships between report nodes; and/or relationships between question nodes.

In one embodiment, the respective data is permanently stored on a server and loaded into the memory of a client at the beginning of the execution of the routine to create the medical report. Afterwards, no or very little communication might be required.

The memory may be a memory that is external to the engine or internal to the engine and preferably stores relationships between question nodes and report nodes. Relationships between report nodes may also be stored in this memory, although it is possible that these are stored in a different memory. Relationships between question nodes may also be stored in the memory associated with the engine although it is possible that these are stored in a different memory. Providing these relationships allows the engine to quickly identify which of the report nodes are affected by an input of a specific question node.

In one further embodiment, at least one report node, preferably at least one text template of at least one report node, comprises and/or is associated with at least one function, the output of the function depending upon the input of at least one question node, wherein, upon receiving an input related to a question of the question nodes, the engine is preferably adapted to at least partially solve the at least one function based on the input of the respective question node.

Providing functions within text templates means that certain inputs can be adapted for insertion into the text template. That is, the function may transform an input into an appropriate output to be inserted into a sentence. This is relevant primarily for linguistic reasons such that a text template can be presented in a grammatically correct fashion. The functions, however, are not limited to linguistic functions and may also be mathematical, i.e., return an output calculated on the basis of a numerical input. The output could be numerical, text based, or be image based (e.g., medical sketches that, in some embodiments, may be manipulated by the inputs).

In one embodiment, there are many functions. At least one of the functions may perform a 1-to-1 mapping between input and output values. The output values of the function can be text. In a preferred embodiment, at least one of the output values of at least one function comprises a further function. The further function can be evaluated at runtime, e.g. by the engine. This allows processing of input data in a recursive manner. Very complex functions can be implemented with a very simple structure. Also, the readability of the outputted text can be improved by applying this inventive technique. The further function can be evaluated once outputted by the (parent) function. Alternatively, the function might require further input from the question nodes. Thus, the engine might evaluate the further function once all the necessary input values are inputted.

In another, further embodiment, at least one report node is adapted to receive free text, the engine adapted to receive the free text as an input and, on the basis of the input, update the at least one report node, in particular the text template of the at least one report node.

When a question requires text to be manually inserted by a user, such as the specification of a date for example, the engine may obtain the input and subsequently update the report node. This may include simply inserting the text 25 into a blank space of the text template, in a similar manner to the functions described above. Alternatively, the text template of the report node may be "empty", and the free text can be used to fill in this report node. The input could be stored in the report node itself, or in the memory of the engine.

In an additional or alternative embodiment, each report node tree may comprise at least one logical report node, wherein preferably, the logical report node is related to at least one child report node with an associated text template.

The logical report nodes may be disposed in the report node tree so as to provide instructions on how various text templates are linked. The logical report node may have an active property associated therewith, that indicates whether the node is active or not (i.e., operational or not operational), wherein this property may be changed by the engine. Additional properties may also be assigned to the logical nodes. The logical report node may contain the 40 instructions to enable the engine to identify whether or not a text template of a child node should be displayed. Logical nodes may also be linked together such that, when an active property of one logical node is changed to not active, the active property of all nodes that depend from this logical report node may also be changed to not active. This may cause the text templates associated with any of the logical nodes, either directly or via children nodes, to change their visibility property, preferably to hidden.

The engine is adapted to receive a first set of inputs related to question nodes of a branch of the question tree, a branch of the question tree comprising a plurality of concatenated question nodes each related to at least one question node of the branch, and wherein the engine is further adapted to change a/the visibility property of affected report nodes associated with the question nodes of the branch based on the first set of inputs and, in response to a change of one of the inputs of the first set of inputs, the engine is adapted to change the visibility property of at least one report node corresponding directly to the changed input, in addition to any report nodes depending from the at least one report node corresponding directly to the changed input.

The visibility properties of report nodes may be linked such that the visibility properties of any report nodes depending from a first report node are changed in correspondence with a change in visibility of the first report node. Preferably, this is only applicable if an input has already been received for these report nodes, i.e., that form the first set of inputs. In one arrangement, the engine is adapted to identify each report node that subsequently depends from a first report node. In other embodiments, logical report nodes may be used to link report nodes and are adapted to regulate their own active and visibility properties. This is useful if a user changes the input to a question such that text that is no longer relevant can be hidden from view.

In an embodiment, preferably a further adaptation of the embodiment above, the question and/or report node trees are adapted to store the received inputs, wherein, when a/the changed input is changed back to that given in a/the first set of inputs, the engine is adapted to change a/the visibility property of at least one report node corresponding to the changed input, in addition to report nodes depending from the at least one report node and which have a corresponding stored input.

In this way, inputs that have already been input by the user are stored even if these inputs are no longer relevant based upon the inputs relating to previous question nodes. The inputs could be stored in a memory associated with the question tree or report node tree. Preferably, the inputs are stored within the nodes of the respective trees. Therefore, when a user changes their answer to a question that they have already changed, any previously provided inputs to question nodes that depend from that question node will be displayed when the input is received. This avoids needlessly re-entering information if a user accidently answers a question incorrectly.

In a further embodiment, an input to at least one question node of the question tree causes duplication of question nodes depending on the at least one question node.

Preferably, the question tree is provided in a complete form, i.e., all the questions are present and no additional question nodes are created. However, in some cases, duplication of question nodes may be necessary. In this case, when an input is received by the engine, the engine may be adapted to duplicate the question nodes in accordance with the input. This may be directly, i.e., the engine performs the duplication, or indirectly, i.e., the engine instructs another entity to perform the duplication. The duplication is preferably based upon template question nodes that do not form part of the question tree per se, i.e., they are not accessible by answering questions. A similar action may also occur with regards to the report node tree; In this case, however, the report nodes may also be sorted with respect to a question node number. This reduces processing time when duplication is required, as the nodes are already present and can simply be copied, rather than being created from scratch.

The apparatus may also further comprise question tree generation means adapted to generate the question tree including question nodes on the basis of the plurality of questions, a plurality of answers related to the plurality of questions, question relation identifiers relating any of the plurality of question nodes to at least a second question node, and input type identifiers indicating a possible input type for each question node; and report node tree generation means adapted to generate the report node tree including the plurality of report nodes on the basis of question-report node relation identifiers, which relate one or more of the plurality of report nodes to one of the plurality of question nodes.

The question tree generation means and the report tree generation means may generate the tree data structures on the basis of raw inputs, i.e., questions, answers, and text templates. The nodes may subsequently be linked depending upon the specific structure to be used. This provides a means for generating the trees for a variety of different input parameters.

In one embodiment, the question tree generation means further comprises: node generating means for generating at least one question node by assigning at least one selectable answer or character entry element to each of the plurality of questions on the basis of input type identifiers indicating the possible input type for each question node; question assigning means for assigning a second question node to the at least one selectable answer or character entry element of a selected question node on the basis of the question relation identifiers; and output means for outputting the question tree on the basis of the output of the node generating means and the output of the question assigning means.

In one embodiment, the report node tree generation means comprises:

report node generation means for generating the plurality of report nodes, wherein at least one report node is related to another report node;

node updating means for updating at least one report node containing a text template on the basis of a corresponding received input, wherein the input is stored either directly or indirectly in the report node; and output means for outputting the report node tree on the basis of the output of the report node generating means and the output of the node updating means.

The report node tree generation means may comprise a report node generation means which produces report nodes that corresponding to the questions of the question tree, wherein at least one report node is dependent upon another report node. In one arrangement, the report node tree is generated on the basis of identifiers relating text templates and/or logic to one another. It may be that the report node tree is additionally generated on the basis of identifiers relating text templates and/or logic to questions of the question tree. In this sense, the report node tree may be similar to the question tree, although this very much depends upon the nature of the question being asked.

Moreover, node updating means may also be provided, wherein the node updating means takes an input received into the apparatus, i.e., from a user, and modifies the report node on the basis of this. This may include, for example, altering the text template corresponding to the report node. For example, the text template may include a function, or may be a blank text string, and when the input is received, the node updating means may alter the text template accordingly, e.g., inserting the output of the function or inserting the input into the text template. The completed or updated report node tree may be output by the output means.

A further embodiment may comprise an interface for displaying the question tree and for receiving the report node tree, wherein a/the visibility property of each report node of the report node tree is initially set to hide the report nodes from view, and adapted to receive the inputs from a user and forward the inputs to the engine.

In yet another embodiment, a first database for storing a plurality of question nodes and a second database for storing a plurality of report nodes are provided, wherein the question tree and report node tree are formed on the basis of a template identifier, the template identifier indicating a first set of question nodes and a corresponding first set of report nodes.

Such an arrangement offers complete customisability for a user, in that a template identifier determines which questions for the database are relevant to a specific medical report. A user can select a template identifier and generate the relevant question nodes for the question tree, and likewise for the report node tree, in order to create a desired medical report. Preferably, both databases may be located on the server.

The problem is also solved by a method for electronically producing at least a part of a medical report, the method comprising:

providing a report node tree (RN) comprising a plurality of report nodes, wherein at least one of the report nodes comprises and/or represents a text tem plate;

providing a question tree (Q), the question tree (Q) comprising a plurality of question nodes, at least some of the question nodes representing a question, wherein at least one of the questions is related to and depends upon the answer of another of the questions;

receiving inputs, at least one of the inputs relating to the question of a selected question node of the plurality of question nodes, storing the input in the selected question node and/or associated therewith, identifying at least one affected report node associated with the selected question node, changing a property, in particular a visibility property, of the at least one affected report node, and preferably, inserting and/or storing the received input in either the at least one affected report node and/or the selected question node.

The problem is also solved by a computer readable device comprising instructions that, when executed, perform the method above.

These and other aspects of the invention will be apparent from and elucidated with reference to the embodiments described hereinafter.

In the following drawings:

FIG. 2a shows an exemplary question tree;

FIG. 2b shows an exemplary relationship table for the question tree of FIG. 2a;

FIG. 3b shows an exemplary relationship table for the report node tree of FIG. 3a;

Figure 1:
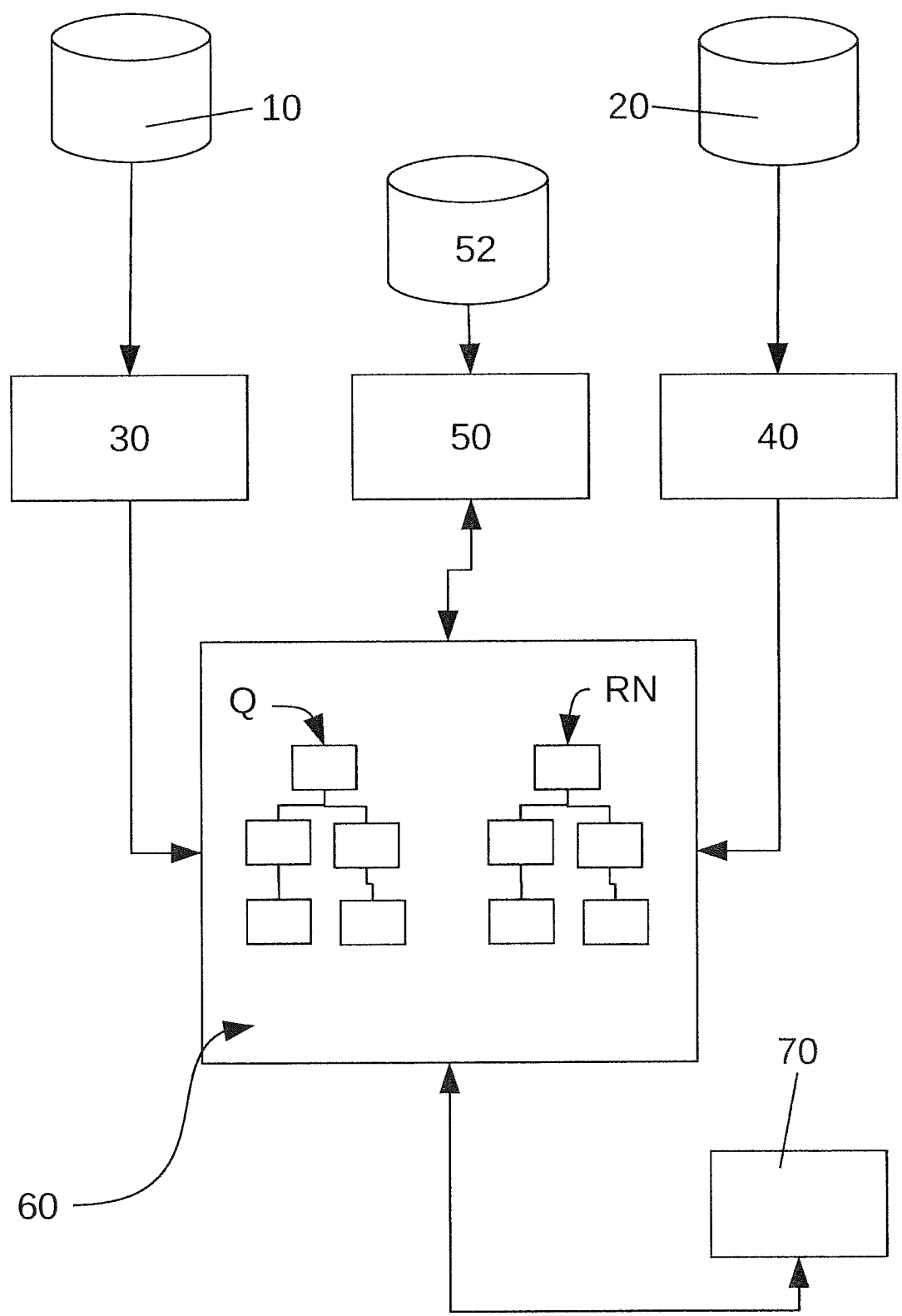
FIG. 1 shows an exemplary arrangement of the apparatus for producing a medical report according to the present invention.

FIG. 1 shows an exemplary arrangement for realising the present invention. The apparatus of the present invention includes a question tree Q, a report node tree RN, and an engine 50. The question tree Q is presented to a user of the apparatus, preferably via an interface 60.

The question tree Q includes a plurality of question nodes. Preferably, each question node of the question tree Q is associated with a question; however, it is also possible that only some of the question nodes are associated with questions. In some embodiments, the questions are text-based, but may additionally or alternatively include image-based questions depending upon the question to be asked.

Preferably, at least one of the questions is related to and depends upon the answer to another of the questions. In other words, a second question is only relevant depending upon the answer to a first question. For example, a first question could be "is a tumour present?" to which the second question "How big is the tumour?" is only relevant if the answer to the first question is YES. In this case, the second question is related to the first based upon one of the answers to be given, i.e., only YES and not NO. It is also possible, however, that a second question is related to the first question regardless of the answer to the first question.

Figures 2A, 2B:
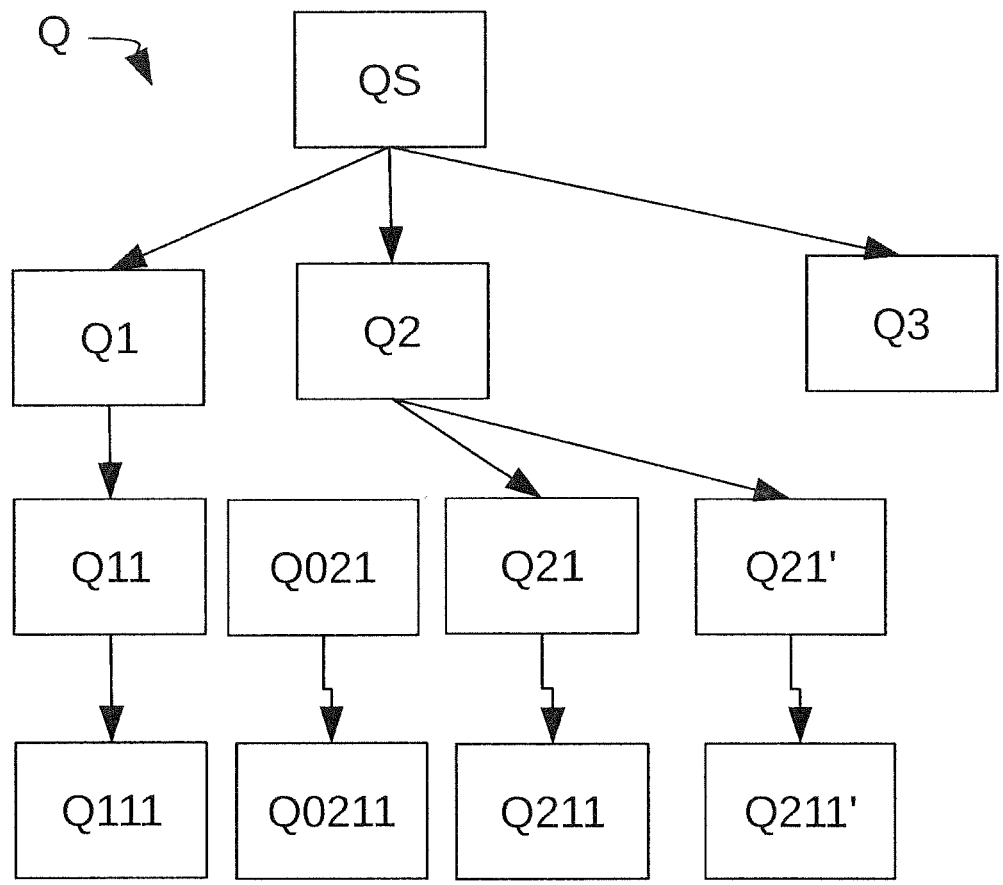

Therefore, the question tree Q contains a plurality of question nodes, some of which are related. It should be appreciated that this relation leads to a tree-type data structure being formed, with a number of branches stemming from various question nodes. FIG. 2a discloses an exemplary question tree Q. The number of branches of the question tree Q is not limited and may vary depending upon the set of questions used to form the question tree Q.

As described above, preferably each question is also associated with at least one answer. The answer may take any form depending upon the question.

The question tree Q is preferably displayed to a user of the apparatus. In one embodiment, the question tree Q is displayed via an interface 60, as shown in FIG. 1. In this regard, the interface 60 can display the question tree Q in any format as desired. In one arrangement, the nodes of the question tree Q may be displayed wherein the question nodes contain the questions therein. Alternatively, the question nodes may simply include a link to the respective questions. The questions may be stored in a first database 10 and may also be stored along with corresponding answers. In either case, the question tree Q is preferably displayed in a condensed form; that is, parent question nodes that have one or more child question nodes are displayed initially, while the child question nodes are hidden. Providing an answer to the parent question node may cause the child question nodes to be displayed. That is, some question nodes may be initially visible when the user begins creating the medical report, with others hidden from view. In some embodiments, a question tree appearance means may be used to alter the appearance of the question tree Q on the interface 60.

In a preferred arrangement, the question tree Q is provided in a complete manner. That is, the entire question tree Q is accessible once provided to the interface 60. In some cases, however, certain branches of the question tree Q may need to be duplicated. For example, if the question requires a number to be entered, e.g., "How many suspect lymph nodes are there?", a separate branch may be created depending upon the numerical value.

An example of this is seen in FIG. 2a. In this case, Q2 may require a value to be inserted, in answer to the question above for example. If the number is two, then a first branch (Q21, Q211) may be created relating to the first lymph node, and a second branch (Q21', Q211') may be created relating to the second lymph node; in each case, the question nodes of the branch are identical. In one implementation, a template branch may be provided, wherein the template branch includes a number of question nodes that are never used themselves; in FIG. 2a, this includes Q021 and Q0211. Using this template branch, a certain number of branches can be created and added to the question tree Q by duplicating the nodes of the template branch.

The report node tree RN includes a number of report nodes. The report nodes can take many forms as will be discussed in more detail below, but at least one of the report nodes includes a text template. The text template may be one or more sentences of text, wherein a sentence ranges from one to many characters. These sentences of text may be complete sentences, or may be sentences with just one single character (incl. letters, punctuation or blank spaces) therein. These blank spaces may be occupied by one or more additional elements of text provided in relation to one or more questions. It should also be appreciated that the text template may also contain numerical values or characters. Some report nodes may also include graphics or the like as the text template, or graphics may be provided as part of a text template in combination with text.

Figure 3A:
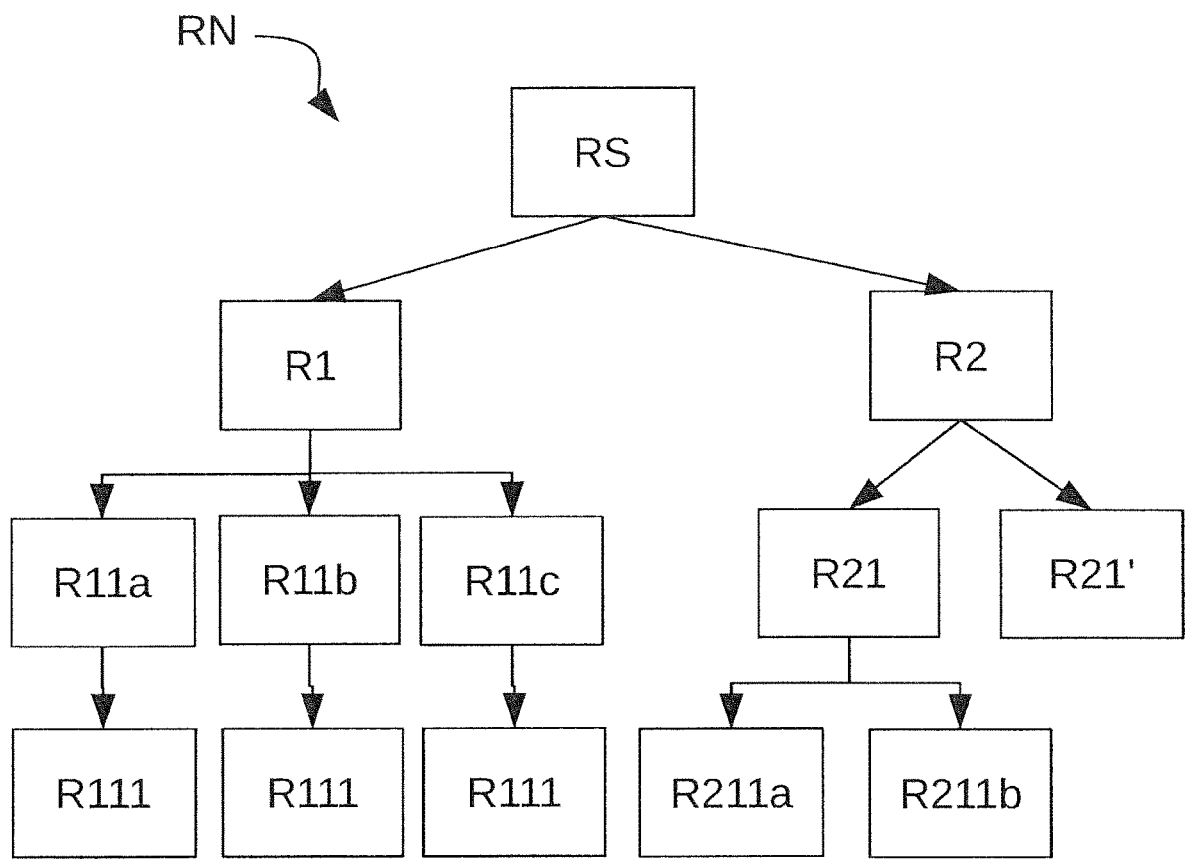
FIG. 3a shows an exemplary report node tree.

The report node tree RN is also preferably provided in a tree-like data structure, much like the question tree Q. That is, some of the report nodes may be linked and relate to other report nodes. This is particularly the case when the text template of one report node is to be inserted into the text template of the previous report node. FIG. 3a shows an example of a report node tree RN.

The report node tree RN may also be provided to the user, preferably via the interface 60. However, unlike the question tree Q, the report nodes of the report node tree RN are initially typically provided hidden from view. That is, the report node tree RN may be created and may then be provided to the user interface 60, but the report nodes are not visible to the user at this time. In this regard, each report node may be provided with a property, particularly a visibility property, that indicates if the report node is to be displayed or not. The property may be indicated or assigned in any way to the report nodes; for example, by a marker or a flag. In some cases, all the report nodes are initially hidden from view. In other cases, some report nodes may be initially visible when the user begins creating the medical report.

The engine 50 is responsible for dynamically creating the medical report, or at least a part of the final medical report. The engine 50 receives inputs from the user, preferably via the interface 60, wherein at least one of the inputs corresponds to a question of a specific question node. Generally, the inputs relate to answers of the questions, although this may not always be the case. For example, the input may relate to display properties of the medical report, i.e., the brightness or font used. It should also be noted that a plurality of inputs may also be specified for the same question node, for instance, when multiple elements from a list are to be selected.

The engine 50 may also store the inputs received. The inputs could be stored in a number of locations. In one embodiment, the inputs may be stored in the question nodes of the question tree Q. That is, the engine 50 may update the question nodes to include an indication of the input. Additionally, or alternatively, the inputs could be stored in a memory 52. FIG. 1 shows the memory 52 as a separate component, however the memory 52 could also be integrated with the engine 50.

On the basis of the input, the engine 50 identifies related report nodes of the report node tree RN. That is, the engine 50 locates at least one report node that corresponds to the question node. Moreover, the engine 50 further determines which of the report nodes are affected by the input relating to a question node. That is, for example, suppose question node Q11 of FIG. 2a relates to a question that includes three options—for example, the type of scan performed such as CT, MRI, etc. In FIG. 3a, report nodes R11a, R11b, R11c, may include text templates relevant to each of the three options. Therefore, when the engine 50 receives an input of "CT" as an input for question node Q11, the engine 50 identifies the relevant report nodes, for example R11a to R11c, and sets (or confirms) the relevant visibility property—in this case, that R11a is set to visible, and R11b and R11c are set to hidden. Alternatively, the engine may only identify and operate on report node R11a, and not report nodes R11b and R11c.

In order to identify the relevant report nodes, the engine 50 may also be provided with a memory 52 for storing a plurality of relationships, in a relationship table for example. The memory could be a different memory to memory 52 for storing the inputs, but is preferably the same memory 52. Ideally, the relationships include a relationship between a question node and one or more report nodes. To implement this, each question node may be provided with a question node identifier QuID and each report node may be provided with a report node identifier RnID. The question node and report node identifiers QuID, RnID are not limited to any format and can be specified depending upon the nomenclature to be used.

In addition, a condition may also be stored, wherein the condition indicates when the relationship is true (or false) for example. That is, if the relationship is valid only when the answer to the question of the question node is YES, then the condition stored is a YES. Therefore, an input indicating the question node identifier QuID, for example Q11, and the answer to the question of the question node, for example "CT", the engine 50 is adapted to consult the relationship table and identify that, in this case, R11a is the relevant report node. Of course, more than one report node may be related to a question node.

In some cases, the question node identifier QuID may be configured to indicate the answer to the question of the question node simply by the choice of identifier. That is, each possible answer to a question is assigned a question node identifier QuID. This may, typically, lead to more than one question node identifier QuID being assigned to each question node, whereby the appropriate question node identifier QuID is received and used by the engine 50.

The engine 50 is further adapted to change a property of the identified report node. In a preferred embodiment, the engine 50 changes a visibility property of the identified report node, whereby the visibility property indicates that the text template of the report node can be either hidden or displayed. Using the example above, when report node R1 is the identified node, the engine 50 changes the visibility property of the report node R1 to display the text template of the report node R1, more specifically, at the interface 60.

In this way, the present invention can dynamically produce a medical report. By answering a question, the engine 50 locates at least one affected report node and, depending upon the action to be taken, changes the property of the affected report elements. That is, sections of text, i.e., the text template of a certain report node, are switched from a hidden state to a displayed state.

Accordingly, a user can dynamically build a medical report by answering the questions of the question tree Q in such a way that only the relevant elements of the report are displayed at any one time. This means that the user is not faced with selecting multiple text templates to be displayed, or manually identifying and/or typing text to form the report.

With reference to FIGS. 2a, 2b, 3a, and 3b, the relationship between the question tree Q and report node tree RN will be described more fully. It is stressed, however, that the specific relationships and questions used in these figures are exemplary only, and are provided only for a better understanding.

As stated previously, the question tree Q includes a number of questions that may be represented by question nodes. These question nodes may also be interrelated in accordance with the dependence of the questions.

Referring to FIGS. 2a and 2b, one can see that Q1 is a parent question node and has a child depending therefrom, Q11, and a grandchild Q111. As seen in FIG. 2b, question node Q11 could be a YES/NO based question; for example, "Was a scan performed?" This is indicated by the input type identifier InID of FIG. 2b, which essentially provides the format that the input provided by the user in response to the question is to be expected. On the basis of the input type identifier InID, the question nodes may also be provided with an appropriate selectable element, such as a selectable "tick" or "YES" provided on the interface 60, or with a character entry element for inserting one or more characters as a response—in this case a "Y" to signify YES, for instance.

FIG. 3b shows an exemplary relationship table that may be referenced and used by the engine 50 to identify the report node in response to an input associated with a question node. In the Fig., report node R1 is seen to correspond to question node Q1. One can also identify that the condition, i.e., YES or NO, determines the action to be applied to the report node. Specifically, the YES input causes the report node R1 to be displayed, while the NO input causes the report node R1 to, in this case, remain hidden.

In some cases, the report node contains a text template, wherein the text template is displayed or hidden. In this example, the text template of report node R1 could read as "A #1 scan was performed on #2." Clearly, in this example, if the input to question node Q1 is negative, i.e., NO, the text template of report node R1 should not be displayed. As the report nodes and text templates therewith are initially hidden, providing a NO input for question node Q1 means that the engine 50 takes no further action for this question, i.e., it does not change the visibility property of this report node.

In contrast, when the input is positive, i.e., YES, the engine 50 identifies that a property of the report node R1 is to be changed; specifically, that a visibility property is to be changed to indicate that the text template is to be displayed.

After the input to question node Q1 is received, two actions preferably occur. Firstly, the report node tree RN is updated by the engine 50 to display the text template and, secondly, question node Q11 is displayed. The input, i.e., the YES answer, may be stored either in a memory 52, for example, integrally provided with the engine 50, or preferably in the question nodes themselves. That is, the engine 50 may be adapted to update a property, namely an answer property, of the question node.

From FIG. 2b, one can identify that question node Q11 is related to question node Q1 and, moreover, that this relationship is true or realised only when the input (or answer) to question node Q1 is YES, as indicated by the condition. That is, question node Q11 is only relevant to question node Q1 if the input to question node Q1 is YES.

Question node Q11 includes an input type identifier indicating a list of three elements; in other words, one of three options can be specified as an input to the question node Q11. As described above, the question relating to question node Q11 could be, "What type of scan was performed?" This could be answered in one of three ways, either by "CT", "MRI", or "Different", for example. These three options may be provided as three selectable elements, in a similar manner to that as described above. Specifically, each selectable element may correspond to a report node; R11a, R11b, or R11c, as indicated in FIG. 3b.

In the above example, the text template of report node R1 includes several placeholders indicated by #1 and #2. These placeholders may indicate the presence of a function. In this case, a function may take one or more inputs from one or more different question nodes or text templates from report nodes and operate on the input to create an output. In the example, #1 is related to Q11, meaning that the input to question node Q11 is inserted into a function corresponding to #1 and operated thereon. Specifically, one of the text templates of the report nodes R11a, R11b, or R11c may be inserted into the function. Preferably, any operation is performed by the engine 50—the relationship table may also include an indication of various functions to aid with this. Alternatively, a separate calculation unit may be provided specifically to calculate functions.

The simplest of functions is essentially that the input equals the output, that is, no operation is performed. When CT or MRI is selected from the list, the engine 50 may read the function associated with report node Q1 and insert CT or MRI. In this case, the output of the function corresponding to #1 is the input, so the input or report node is subsequently displayed at the location marked by #1 in the text template associated with report node R1. Alternatively, when the "Different" option is selected, the sentence does not make sense with a capital "D". The function corresponding to #1 may be adapted to replace "Different" with "different". In this case, the engine 50 changes the visibility property of the text template of report node R11 and inserts this into the text template.

It should also be appreciated that any combination of the list elements of question node Q11 could also be provided; for instance, suppose both a CT and MRI scan were performed. In this case, a first input to question node Q11 might indicate CT, and the process above is carried out. When entering the second input of MRI, the engine 50 inserts this into the function corresponding to #1. As a result, the function may cause the input to go from "CT" to "CT and MRI".

Equally, in one configuration, the function corresponding to #1 may be a function of a function. Suppose, for example, that a first function alters the text of the selected element, i.e., "Different" to "different". A second function may take the output of the first function and operate on this output. This may be useful for example when the sentence requires adaption for a plurality of objects. Suppose, as a different example, the text template reads "#1 performed on #2". When the input is only one of the elements from the list, the first function outputs "different" for example, and the second function realises that only one output is present and sets #1 to read as "A different scan was". Alternatively, suppose also that a second input is selected, i.e., MRI. The first function may cause the output to read as "An MRI and a different" and the output of the second function may set #1 to read as "An MRI and a different scan were" in this case. In this way, the sentences of a text template can be readily adapted to account for changes in grammar or sentence structure.

In an alternative embodiment, the text template of report nodes R11*a*, R11*b*, and R11*c* may all be identical, but differ only at the position #1. For instance, R11*a* could read as "A CT scan was performed on #2", while R11*b* could read as "An MRI scan was performed on #2". In this case, selecting both selectable elements leads to both of the above text templates being displayed. In this case, report node R1 may not have any text template associated with it.

In yet another alternative embodiment, the report nodes R11*a*, R11*b*, R11*c* may be logical report nodes and not be provided with a text template. Instead, the logical report nodes may be provided with an active property controllable by the engine 50 to indicate whether or not the logical report node is active or not. In this case, the selectable input provided as one of the selectable answers relating to question node Q11 may implicitly contain a text template, which in this case would be equivalent to the actual text displayed to the user. Therefore, when selected, the engine 50 may simply update the report node tree RN by consulting the logical nodes R11*a*, R11*b*, R11*c* and inserting the text template corresponding to the selected element. The logical report nodes may contain the function and process the selected input accordingly. Alternatively, the logical report nodes may simply indicate the position in the previous text template, i.e., related to Q1, or confirm that the input is appropriate; in this case, any functions may be contained within the text template of the previous question node, i.e., question node Q1.

It should be appreciated that any implementation could be used in order to amend or provide the correct sentence for selectable answers.

Once the input(s) to question node Q11 have been received, question node Q111 may be displayed, as seen in accordance with the example of FIGS. 2*a* and 2*b*. As noted in FIG. 2*b*, any condition of question node Q11 relates the question node Q111 to Q11. In other words, the question node Q111 is always present once any input is provided relating to question node Q11.

The input identifier of question node Q111 indicates free text entry. In this regard, question node Q111 may be provided with a character entry element in order for a user to manually input text or use speech recognition. This free text may be treated as an input. As seen in FIG. 3*b*, question node Q111 is related to report node R111. For example, question node Q111 may represent the question "On which date?" In the example described, the input to the question node Q111 may relate to #2 of the text template of report node R1.

In this regard, free text can be treated in a number of ways. The report node R111 could be provided as an "empty" report node. When free text is provided by the user and sent to the engine 50, the engine 50 may update and "fill in" the empty report node with the free text. At the same time, the engine 50 may change the visibility property accordingly. Alternatively, the filled-In report node may simply be inserted into the appropriate location (or function) corresponding to #2. In a different configuration, the free text may be associated with a logical report node at R111. This may be implemented in accordance with the techniques relating to logical report nodes described above.

In the above example, #2 may correspond to a date to be inserted by the user. The function may be adapted to receive the input in any form and provide the desired output. For instance, the date could be input in the form "25.11.14" to which "25.11.14" can be output. Alternatively, the date input could be "Nov. 25, 2014" with the output reading as "25.11.14". The function may also be able to identify the closest possible previous date, for instance if the user inputs "Wednesday", the function determines that the closest previous Wednesday may be "19.11.14" and outputs the same. Preferably, however, the input is subsequently stored as discussed above.

As seen in FIG. 2*a*, question nodes Q1, Q11, and Q111 form a branch of the question tree Q. Question node Q1 may be considered as a root question node meaning that the question Q1 is provided and shown initially to the user. Other question nodes, Q2 and Q3, may be provided in a similar manner to Q1. Generally speaking, the branches stemming from Q1 are independent of the branches associated with Q2 and Q3, although this may not always be the case.

Turning to question node Q2, in the example given above, this question node requires a number to be inserted as an input or answer to the question. For instance, the question could be; "How many lymph nodes (or sites) are affected?" In this case, suppose the answer to the question is two. Report node R2, which corresponds to question node Q2, may be a logical report node. In this case, the report node R2 may contain no text template at all, but instead a set of instructions to be read by the engine 50. In this case, as seen in FIG. 3*b*, the instructions may cause the logical node to duplicate, meaning that the input related to question node Q2 causes the duplication of identical question branches of the question tree Q, and subsequently, identical report nodes of the report node tree RN. Again, the engine 50 may change an active property of the logical report node to signify that the logical report node is active.

As mentioned briefly, a template branch of question nodes may optionally be provided, as seen in FIG. 2*a*. This template branch may be used as a basis to essentially copy and replicate the required number of question branches. When the answer to question node Q2 is "two", the branches are replicated or duplicated twice. The template branches are not used or displayed to the user. Therefore, these branches are not actually "connected" to the previous question node. In this way, when the answer to question node Q2 is zero, for example, no branches are replicated and so no branch is displayed—however, the template branch remains present but hidden from view.

A similar scenario may be provided with regards to the report node tree RN. However, it is not necessary to have a "blank" template branch in this case as, primarily, the report nodes are configured as templates initially. In other words, report node R21 is identical to report node R21'—these report nodes may only be changed or altered on the basis of additional inputs from questions depending thereon. In a preferred case, report node R2 may be associated with a function whose result depends upon the answer to question Q2. For example, the answer may be "two", as stated above, and so the output of the function causes two branches to be duplicated. This may also be relevant when the number of lymph nodes is infinite, i.e., there is a disseminate infection. In this case, only one branch may be required, although there are multiple sites of infection. Therefore, the function can be set to output the correct number of branches required.

In some cases, a text template may also be provided with report node R2. For example, the text template may be "There are #1 suspected lymph nodes (or sites)," wherein, #1 may correspond to a function that inserts the number of lymph nodes in accordance with the input received.

Once the question branches have been duplicated, the user then proceeds to answer the questions of the question nodes accordingly. FIG. 2*a* shows that the input to question node Q21 is a list of five selectable elements. An example question associated with question node Q21 (or Q21') might be "Where is the #1 suspect lymph node?" In this case, the function corresponding to #1 may output the characterising name of the lymph node, i.e., first, second, etc. This function is thus dependent upon the previous question, and it may be that the engine 50 is able to update the question node using the input accordingly. In other cases, the question may be a generic question for each duplicated branch, i.e., "Where is the suspect lymph node?"

The text template of report node R21 may be input with a selected input from question node Q21. For example, the inputs could be "left leg", "right leg", "left arm", "right arm", "torso or head". In this case, unlike with question node Q11, only one input should be selected. In FIG. 3*b*, it can be seen that the condition is "ListFree" meaning that any of the selections from the list cause the text template of report node R21 to be displayed. This may also be provided with a function whereby the location inserted into the text template associated with report node R21.

Question node Q211 is related to question node Q21 when any input is received in relation to Q21, as indicated in FIG. 2*b*. Question node Q211 is provided with an input type of "+1, 0, −1". This input type essentially provides a positive response (+1), a negative response (−1), or an optional response (0). Typically, the optional response will simply mean that the question is ignored and no text template is displayed, although this may not necessarily be the case. In this case, the +1 response may cause the text template of report node R211*a* to be displayed, while the −1 response may cause the text template of report node R211*b* to be displayed. In some cases, other input types may also result in no text being displayed. For example, a question node may state, "Pleural effusion", with the answers given in a list as follow: (A) "Do not report"; (B) "No pleural effusion"; (C) "Low-grade"; (D) "Intermediate grade"; (E) "High grade". In this case, selecting option (A) will not display any text at all, while option (B) will generate text saying. "There is no pleural effusion", for example. In this case, option (A) may either be not displayed (that is, the text template visibility property is set to hide even though an answer is provided), or the text template is displayed but is displayed as a blank character.

Regarding numerical answers, the input may either be selected from an infinite list or simply provided as free text. Alternatively, upper and lower limits may be provided to restrict the user from entering an inappropriate number.

In a preferred embodiment, the duplicated branches may subsequently be reordered depending upon the answer given, in this case, to question Q21 or Q21'. As a different example, suppose question Q21 and Q21' now state, "How big is the infected site?", for example. Assume that the answer is in the form of, a list of "Very large, Large, Medium, Small, Very small". In answer to Q21, the user may select "Small". In answer to Q21', the user may select "Large". In the overall medical report, it may be preferable to arrange the corresponding text templates according to the largest to smallest size—that is, the text templates associated with Q21' should be arranged before the text templates associated with Q21. In one arrangement, the report node tree RN may include a logic report node adapted to organise branches. In other words, this logic report node may compare the answers to Q21 and Q21' and, if appropriate, organise the branches. This may involve renaming or transferring the inputs of the branches, i.e., Q21 goes to Q21' while Q21' goes to Q21, although the method of organisation is not limited to this.

Of course, it should be appreciated that any structure and any questions may be asked depending upon the logical structure to which the questions would normally be asked during preparation of a medical report.

In a preferred implementation, sections of the report may be changed from displayed to hidden on the basis of a different input. That is, text templates of the report may be hidden if already displayed on the basis of an alternative input. Suppose, for example, that Q2 is answered as TWO, which produces two branches involving Q21 and Q21'. Assume Q21' is answered as "left leg". Now suppose that the user made a mistake and, actually, the answer to question Q2 should have been "ONE". The text template relating to Q21' is changed to be hidden by the engine 50 upon receipt of the new input relating to Q2, i.e., an input of ONE. That is, the engine 50 changes the visibility property of Q21' and any report nodes depending upon this node, i.e., Q211'. In this case, any text templates that are displayed to the user at the interface 60 corresponding to these question nodes are removed from view.

Preferably, however, the inputs to question nodes are stored, as discussed above. This means that, should the user realise that actually they were initially correct in that the answer to Q2 is actually "TWO" rather than the changed answer of "ONE", the inputs to Q21' and Q211' have already been stored when initially answered. Therefore, when the user inputs "TWO", the engine 50 is preferably adapted to display the text template associated with report node Q21', including the answer given to Q21' previously, i.e., "left leg", and any text templates and answers relating to Q211'. In this way, a user can quickly and efficiently edit the medical report without losing or having to re-enter inputs Into the interface 60.

The root question nodes may be associated with a template identifier, seen in FIG. 2*a* as QS. This is not necessarily a question node per se, but indicates a general framework for the question tree Q. In this regard, a user may select one or more of a number of different template identifiers. For instance, one template identifier may relate to a medical report for breakages of bones, while another may relate to a medical report for cancer. In this regard, the first database 10 may be provided for storing a plurality of questions, wherein the questions may be related to one or more of the template identifiers. Answers may also be stored with the questions such that each question is associated with one or more possible answers. Upon selecting a template identifier, the relevant questions from the database 10 may be extracted and used to form the question tree Q. Similarly, text templates or instructions for report nodes may be stored in a second database 20 and may also be linked to the template identifier. These text templates and instructions may be extracted in the same way as the questions and used to form the report node tree RN.

It should also be appreciated that more than one template identifier may be selected for each medical report. In this case, a question tree Q and a report node tree RN may be generated for each of the template identifiers. That is, a first question tree Q may relate to broken bones, while a second question tree Q. Independent of the first, may relate to head injuries. These question trees Q can be answered independently of one another. Corresponding report node trees RN may also be provided.

It should also be appreciated that, in some cases, questions may relate to more than one template identifier, in addition to the text templates or instructions for the report nodes. Preferably, the questions are duplicated for each question tree Q and report node tree RN. In some cases, it may be that the same question appears on two different question trees Q of the same report. In this case, it may be that answering one question causes the second instance of the question to be answered in the same way. However, it may be advantageous in such a situation to leave the report node corresponding to the second instance of the question hidden from view until such a time as a question from which it depends is answered.

In order to generate the question and report node trees Q, RN, the apparatus may optionally also include question tree generation means 30 for generating the question tree Q, and report node tree generation means 40 for generating the report node tree RN.

Figure 4:
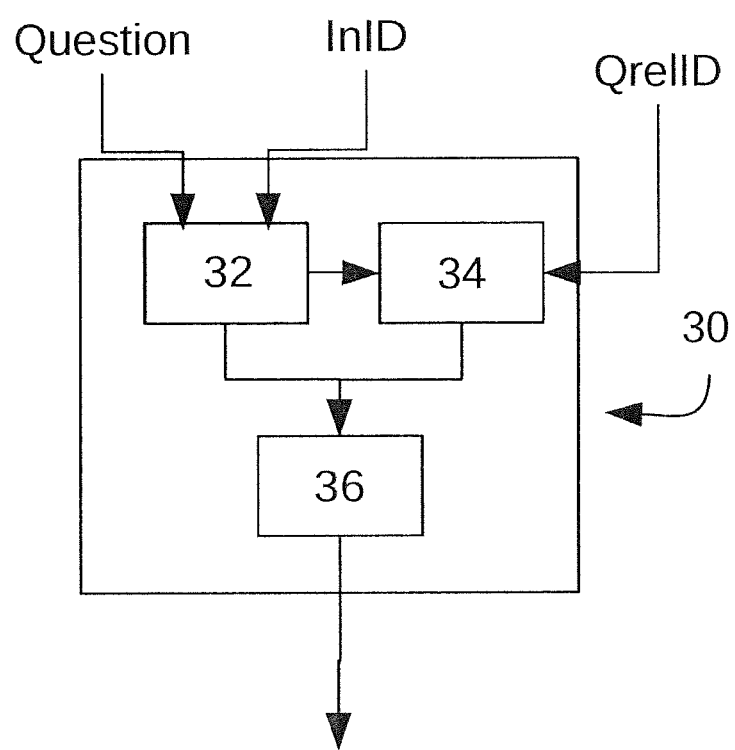
FIG. 4 shows an exemplary arrangement for the question tree generation means.

As seen in FIG. 4, the question tree generation means 30 preferably includes node generating means 32, a question assigning means 34, and output means 36. The node generating means 32 receives question text or images, preferably from the first database 10. In addition, an indication of the input, i.e., the input type identifier InID, may also be provided. Using this information, the node generating means 32 generates a number of question nodes to be used in the question tree Q and may also assign each question node a question node identifier QuID. As a result, each question is provided with a question node and a corresponding answer to be selected in an appropriate format. In some cases, not all question nodes relate to questions. However, text of these question nodes may be treated in the same manner as the question text or images above, and may be stored with the questions in the first database 10. In other words, even if there is no question, a question node may still be created.

The question assigning means 34 preferably obtains the question nodes generated by the node generating means 32 and assigns relationships between the question nodes. This may be based upon question relation identifiers QrelID, which can be provided from the first or second databases 10, 20. Preferably, the question relation identifiers QrelID relate the questions (not question nodes) to each other and indicate the parent question. For example, the question relating to question node Q11 is the child of question node Q1. Thus the question relation identifier QrelID for question node Q11 may be the question corresponding to question node Q1. Optionally, it may be that the question relation identifiers QrelID also include a condition, i.e., upon which answers they are related. The question assigning means 34 therefore outputs a number of question node relation identifiers QNrelID indicating the relationships between the generated question nodes, optionally in combination with a condition relationship. In this regard, question node relation identifiers QNrelID may be equivalent to question relation identifiers QrelID, particularly in a simple arrangement, or they may be different. The question node relation identifiers QNrelID are used by the engine 50 once the question tree QN is established. Question relation identifiers QrelID are used to identify questions for generating the question tree QN. For example, using Q211 and Q211' as discussed above, the question relation identifier QrelID is equal in both cases as both ask the same question—i.e., the question corresponding to Q21 and Q21' is the same. For example, the question of question nodes Q21 and Q21' may be given the global assignment of #01243 in a database containing a plurality of questions. However, Q211 is only related to Q21, not to Q21'. Therefore, the question relation identifier QrelID of Q211 is #01243, but the question node relation identifier QNrelID is Q21.

The output from the output 36 is essentially the question tree Q in a complete form, aside from any duplication procedures that may take place when answering the questions. The output means 36 may receive the question nodes from the node generating means 32 in addition the question node relation identifiers QNreIID and generate the complete question tree Q.

The report node tree generation means 40 may receive the text templates and instructions from the second database 20. The report node tree generation means 40 preferably creates a number of report nodes incorporating the text templates, as well as optionally providing logical report nodes. This can be performed by node generating means which may use a text template relation identifier TxrelID that relates various text templates in a similar way to the question relation identifiers QrelID, and/or text template logic node relation identifiers TxLNrelID that relates logic report nodes to the text templates. Alternatively, and preferably, this is performed using identifiers relating text templates and/or logic to questions of the question tree Q. In this way, the report node tree RN can be created depending upon relationships between the text templates. Additionally, node updating means 44—for report nodes containing a text template may also be provided. On the basis of a corresponding received input, the node updating means 44—may alter the text template and/or logic of a corresponding report node. For example, this may include inserting the input into a text string, inserting the output of a function into a text string, or altering an image. Other updating operations are also possible. In this case, the input is stored either directly or indirectly (i.e., as an output of a function) in the report node.

The report node tree RN may be output by output means. Additionally, the report node tree generation means 40 may assign report nodes to question nodes on the basis of question-report node relation identifiers Q-RNrelID, whereby each question of the question tree Q may be related to one or more report nodes (including logic report nodes) of the report node tree RN.

In some embodiments, the question tree generation means 30 may also be provided with a question tree appearance means 38—which is adapted to display and/or hide various parts of the question tree Q at the interface 60. For example, some of the questions of the question tree Q are concatenated and, initially, only the first of these questions may be displayed. Either by providing an input, or by selecting a visible option, the hidden questions can be subsequently displayed. The question tree appearance means 38—may take such an input and cause the display of the interface 60 to be updated. Alternatively, this function may be performed by the engine 50.

The engine 50 may use the relationship table, an example of which is seen in FIG. 3b, to perform the necessary actions. This relationship table can be populated by the outputs of the question tree generation means 30 and report node tree generation means 40.

Figure 5:
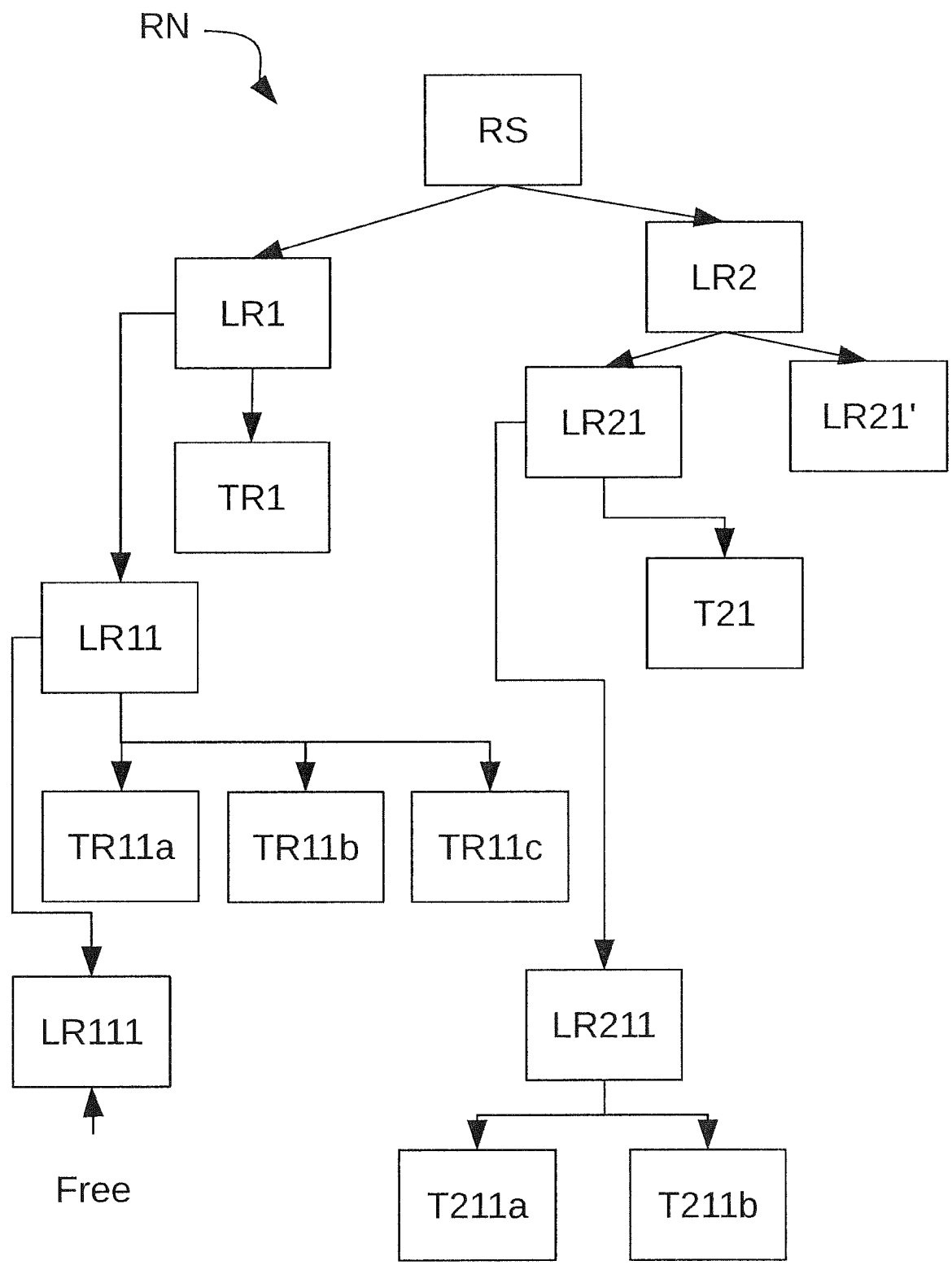
FIG. 5 shows an alternative exemplary question tree.

As described above, in some cases the report node tree RN may include logical report nodes. An example of this is seen in FIG. 5. The node LR1 is a logical report node and corresponds to question node Q1 of FIG. 2a. When an input is received from Q1, the logical report node may be read by the engine 50 to obtain instructions contained in the logical report node LR1. In this case, the instructions may be "Input=Y; Action=Display TR1", wherein TR1 is a text report node that essentially contains the text template of R1 mentioned previously. The engine 50 may then read the instructions and perform the necessary action, in this case by changing the visibility property of the text report node TR1 when the input equals Y. At the same time, the engine 50 may change an active property of the logical report node to indicate that the logical report node is active. Subsequently, when an input is received in relation to Q11, the engine 50 reads the logical report node LR11. As discussed above, three text report nodes TR11a, TR11b, TR11c may be provided. These can either be inserted into the text template TR1, via functions, as report nodes or simply as text entries. As report nodes, the logical report node LR11 determines which report node is displayed depending upon the answer. As text entries, the logical report node LR11 takes the received answer and applies it as the input to the function of TR1—that is, TR11a, TR11b, and TR11c are not provided in this case. Similar arrangements may be provided for other report nodes and these will not be explained in detail herein.

In this report node tree RN, one can see that the logical report nodes are connected, not the text template report nodes. Such an arrangement makes it easier to subsequently hide or display certain branches of the report node tree RN. For example, if the input to question Q2 is different as described above, i.e., from TWO to ONE, the engine 50 may change the property of one of the text report nodes, i.e. TR21', in this case to hidden. Any changes in the visibility property may propagate down the logical node connections, i.e., logical node LR211' may also be adapted to set the visibility property of TR211' to hidden in response to the change in visibility property of TR21'. This may also be possible using the active property of the logical report nodes, is that only if the logical report node is active can the text report node be displayed.

In some cases, the interface 60 may be provided with a reset button. As stated above, the inputs may be stored such that they can be recovered later. However, each question node may be individually reset, thus erasing the input stored within or in association with that question node. Equally, this may also erase the inputs received with nodes that dependent from that node. For example, the input of question node Q11 could be reset which in turn resets the input associated with Q111.

In another embodiment, the apparatus may be provided with report generation means 70. The report generation means 70 is preferably adapted to generate a final medical report on the basis of the currently displayed text templates. In other words, the report generation means 70 takes the text templates currently displayed and, upon receipt of a signal from the interface 60, may reformat the text templates to form the report. This could be useful if, for example, a specific hospital uses certain letter heads and formats and the like. The report generation means 70 may be programmed to format the text templates in accordance with specific requirements. Alternatively, the report generation means 70 may simply output a non-editable version of the report as currently seen on the interface 60.

In some cases, functions of text templates may require inputs from various different questions. These could be displayed initially as text and # identifiers, or these could remain hidden until such a time that all the variables required for the function are present. For example, suppose the report node R21 is also provided with a text template that includes a function for calculating the volume of a tumour. This function may require inputs of width (from Q3), length (from Q4), and depth (from Q5), for example. When Q21 is provided with an answer, various text templates may be displayed; however, the text template including the function may remain hidden. Once all the parameters are provided, the function, which multiples width, length, and depth can be performed. The engine 50 may be adapted to calculate this function using the parameters specified. This could be in real-time, i.e., when the final parameter is input in answer to the question, or upon generating the final medical report. In this sense, rather than display an incomplete text template, the text template can be only displayed once it is completed. This may be particularly useful if, for example, Q5 is never answered or is optional.

The apparatus may be implemented in any fashion. That is, the components may be stored locally on a personal computer or they may be provided hosted by one or more servers. The apparatus may also be adapted to link to other systems, e.g., to a hospital information system (HIS).

The present invention therefore provides an apparatus and method for dynamically producing a medical report, in a user friendly and manageable way. It also provides a user with an indication of what will form the basis of the medical report in real-time, such that the user can adapt and change the form of the report as desired. It also prevents erroneously entering or omitting data as the user must follow a predefined arrangement of questions, as provided by the question tree Q.

REFERENCE NUMERAL LIST

10 First database
20 Second database
30 Question tree generation means 32 Node generating means
34 Question assigning means
36 Output means
38 Question tree appearance means
40 Report node tree generation means
42 Node generating means
44 Text template assigning means
46 Output means
50 Engine
52 Memory
60 Interface
70 Report generation means
Q Question tree
RN Report node tree
QuID Question Identifier
RnID Report node identifier
InID input type identifier
QrelID Question relation identifier
QNrelID Question node relation identifier
Q-RNrelID Question-report node relation identifier
TxrelID Text template relation identifier
TxLNrelID Text template logic node relation identifier

The invention claimed is:

1. An apparatus for electronically producing at least a part of a medical report, the apparatus comprising:
a memory for storing:
a question tree (Q), the question tree (Q) comprising a plurality of question nodes, at least some of the question nodes representing a question, wherein at least one of the questions is related to and depends upon an answer of another of the questions, and
a report node tree (RN) comprising a plurality of report nodes, wherein at least one of the report nodes comprises and/or represents a text template; and
a personal computer or server implemented to:
receive inputs, wherein the inputs relate to answers of the questions, and wherein at least one of the inputs relates to the question of a selected question node of the plurality of question nodes,
store the input in the selected question node and/or associated therewith,
identify at least one affected report node associated with the selected question node,
change a visibility property of at least one of the at least one affected report nodes, the visibility property being whether the report node is hidden or fully displayed, and
insert and/or store the received input in either the at least one affected report node and/or the selected question node;
wherein the memory stores a plurality of relationships, the relationships including:
a relationship between at least one question node and at least one report node;
relationships between report nodes; and
relationships between question nodes;
wherein the personal computer or server is adapted to receive a first set of inputs related to answers of questions nodes of a branch of the question tree (Q), a branch of the question tree (Q) comprising a plurality of question nodes that may be concatenated and each related to at least one question node of the branch, and
wherein the personal computer or server is further adapted to change a/the visibility property of affected report nodes associated with the question nodes of the branch based on the first set of inputs and, in response to a change of one of the inputs of the first set of inputs, the personal computer or server is adapted to change the visibility property or active property of at least one report node corresponding directly to the changed input, in addition to any report nodes depending from the at least one report node corresponding directly to the changed input;
wherein the memory stores the received inputs, wherein, when a/the changed input is changed back to that given in a/the first set of inputs, the personal computer or server is adapted to change a/the visibility property of at least one report node corresponding to the changed input, in addition to report nodes depending from the at least one report node and which have a corresponding stored input; and
wherein the personal computer or server is adapted to display at least parts of the text template of at least one report node based on the visibility property of at least one report node, the displayed text template forming at least a part of the medical report.

2. The apparatus of claim 1, wherein at least one report node and/or at least one text template of at least one report node, comprises and/or is associated with at least one function, an output of the function depending upon the input of at least one question node,
wherein, upon receiving an input related to an answer of a question of the question nodes, the personal computer or server is adapted to at least partially solve the at least one function based on the input of the respective question node.

3. The apparatus of claim 1, wherein at least one report node is adapted to receive free text, the personal computer or server adapted to receive the free text as an input and, based on the input, update the at least one report node, by updating the text template of the at least one report node.

4. The apparatus of claim 1, wherein each report node tree (RN) comprises at least one logic report node, the logic report node comprising at least one child report node with an associated text template.

5. The apparatus of claim 1, wherein an input to at least one question node of the question tree (Q) causes duplication of question nodes depending on the at least one question node, wherein, the duplicated question nodes are further sorted according to an input to the at least one question node, or inputs according to the question nodes depending on the at least one question node.

6. The apparatus of claim 1, wherein the personal computer or serer is implemented:
to generate the question tree (Q) including question nodes based on the plurality of questions, a plurality of answers related to the plurality of questions, question relation identifiers (QrelID) relating some of the plurality of question nodes to at least a second question node, and input type identifiers (InID) indicating a possible input type for each question node; and
to generate the report node tree (RN) including the plurality of report nodes based on question-report node relation identifiers (Q-RNrelID), which relate one or more of the plurality of report nodes to one or more of the plurality of question nodes.

7. The apparatus of claim 6, wherein the personal computer or server is implemented:
to generate at least one question node by assigning at least one selectable answer or character entry element to each of the plurality of questions based on input type identifiers (InID) indicating the possible input type for each question node;

to assign at least one second question node to the at least one selectable answer or character entry element of a selected question node based on the question relation identifiers (QrelID); and to output the question tree (Q) based on the at least one question node and the at least one second question node.

8. The apparatus of claim 6, wherein the personal computer or sever is implemented:

to generate the plurality of report nodes, wherein at least one report node is related to another report node;

to update at least one report node containing a text template based on a corresponding received input, wherein the input is stored either directly or indirectly in the report node; and to output the report node tree (RN) based on the plurality of report nodes, and the updated at least one report node containing the text template.

9. The apparatus of claim 1, wherein the personal computer or server generates an interface to display the question tree (Q) and to receive the report node tree (RN), wherein a/the visibility property of each report node of the report node tree (RN) is initially set to hide the report nodes from view, and adapted to receive the inputs from a user.

10. The apparatus of claim 1, wherein the memory comprises a first database to store a plurality of question nodes and a second database to store a plurality of report nodes, wherein the question tree (Q) and report node tree (RN) are formed based on a template identifier, the template identifier indicating a first set of question nodes and a corresponding first set of report nodes.

11. A method for electronically producing at least a part of a medical report, the method comprising:

providing a report node tree (RN) comprising a plurality of report nodes, wherein at least one of the report nodes comprises and/or represents a text template;

providing a question tree (Q), the question tree (Q) comprising a plurality of question nodes, at least some of the question nodes representing a question, wherein at least one of the questions is related to and depends upon an answer of another of the questions;

a personal computer or server receiving inputs, wherein the inputs relate to answers of the questions, and wherein at least one of the inputs relates to the question of a selected question node of the plurality of question nodes, the personal computer or server storing the input in the selected question node and/or associated therewith, the personal computer or serer identifying at least one affected report node associated with the selected question node, the personal computer or serer changing a visibility property of at least one of the at least one affected report nodes, the visibility property being whether the report node is hidden or fully displayed, and the personal computer or server inserting and/or storing the received input in either the at least one affected report node and/or the selected question node;

storing in a memory a plurality of relationships, the relationships including:

a relationship between at least one question node and at least one report node;

relationships between report nodes; and relationships between question nodes;

the personal computer or server receiving a first set of inputs related to answers of question nodes of a branch of the question tree (Q), a branch of the question tree (Q) comprising a plurality of question nodes that may be concatenated and each related to at least one question node of the branch;

wherein the personal computer or sever changes a visibility property of affected report nodes associated with the question nodes of the branch based on the first set of inputs and, in response to a change of one of the inputs of the first set of inputs, the personal computer or server changes the visibility property or active property of at least one report node corresponding directly to the changed input, in addition to any report nodes depending from the at least one report node corresponding directly to the changed input; and storing in the memory the received inputs, wherein, when a/the changed input is changed back to that given in a/the first set of inputs, the engine changes a/the visibly property of at least one report node corresponding to the changed input, in addition to report nodes depending from the at least one report node and which have a corresponding stored input; and wherein the personal computer or serer displays at least parts of the text template of at least one report node based on the visibility property of at least one report node, the displayed text template forming at least a part of the medical report.

12. A non-transitory computer readable device comprising instructions that, when executed by a personal computer or server, perform a method for electronically producing at least a part of a medical report, the method comprising:

providing a report node tree (RN) comprising a plurality of report nodes, wherein at least one of the report nodes comprises and/or represents a text template:

providing a question tree (Q), the question tree (Q) comprising a plurality of question nodes, at least some of the question nodes representing a question, wherein at least one of the questions is related to and depends upon an answer of another of the questions;

the personal computer or server receiving inputs, wherein the inputs relate to answers of the questions, and wherein at least one of the inputs relates to the question of a selected question node of the plurality of question nodes, the personal computer or server storing the input in the selected question node and/or associated therewith, the personal computer or server identifying at least one affected report node associated with the selected question node, the personal computer or server changing a visibility property of at least one of the at least one affected report nodes, the visibility property being whether the report node is hidden or fully displayed, and the personal computer or server inserting and/or storing the received input in either the at least one affected report node and/or the selected question node;

storing in a memory a plurality of relationships, the relationships including:

a relationship between at least one question node and at least one report node;

relationships between report nodes; and relationships between question nodes;

the personal computer or server receiving a first set of inputs related to answers of question nodes of a branch of the question tree (Q), a branch of the question tree (Q) comprising a plurality of question nodes that may be concatenated and each related to at least one question node of the branch;

wherein the personal computer or serer changes a visibility property of affected report nodes associated with the question nodes of the branch based on the first set of inputs and, in response to a change of one of the inputs of the first set of inputs, the personal computer or serer changes the visibility property or active property of at least one report node corresponding directly to the changed input, in addition to any report nodes depending from the at least one report node corresponding directly to the changed input; and storing in the memory the received inputs, wherein, when a/the changed input is changed back to that given in a/the first set of inputs, the engine changes a/the visibility property of at least one report node corresponding to the changed input, in addition to report nodes depending from the at least one report node and which haw a corresponding stored input; and wherein the personal computer or sever displays at least parts of the text template of at least one report node based on the visibility property of at least one report node, the displayed text template forming at least a part of the medical report.

\* \* \* \* \*